United States Patent
Primor

(10) Patent No.: US 9,849,148 B2
(45) Date of Patent: Dec. 26, 2017

(54) MAGNESIUM-CONTAINING PRODUCTS AND USES THEREOF

(71) Applicant: Naveh Pharma (1996) Ltd., Natania (IL)

(72) Inventor: Nitsan Primor, Tel-Aviv (IL)

(73) Assignee: Naveh Pharma (1996) Ltd., Natania (IL)

( * ) Notice: Subject to any disclaimer, the term of this patent is extended or adjusted under 35 U.S.C. 154(b) by 0 days.

(21) Appl. No.: 15/180,142

(22) Filed: Jun. 13, 2016

(65) Prior Publication Data

US 2016/0287629 A1    Oct. 6, 2016

Related U.S. Application Data

(62) Division of application No. 14/194,833, filed on Mar. 3, 2014, now abandoned.

(Continued)

(51) Int. Cl.
| | |
|---|---|
| *A61K 33/08* | (2006.01) |
| *A61K 31/355* | (2006.01) |
| *A61K 31/4415* | (2006.01) |
| *A61K 31/593* | (2006.01) |
| *A61K 9/00* | (2006.01) |
| *A61K 9/16* | (2006.01) |
| *A61K 9/20* | (2006.01) |
| *A61K 9/28* | (2006.01) |

(Continued)

(52) U.S. Cl.
CPC ............ *A61K 33/08* (2013.01); *A61K 9/0053* (2013.01); *A61K 9/16* (2013.01); *A61K 9/2027* (2013.01); *A61K 9/2054* (2013.01); *A61K 9/28* (2013.01); *A61K 31/355* (2013.01); *A61K 31/4415* (2013.01); *A61K 31/593* (2013.01); *A61K 31/675* (2013.01); *A61K 45/06* (2013.01)

(58) Field of Classification Search
CPC .. A61K 33/08; A61K 2300/00; A61K 31/355; A61K 31/4415; A61K 31/593; A61K 31/675; A61K 45/06; A61K 9/0053; A61K 9/16; A61K 9/28
See application file for complete search history.

(56) References Cited

U.S. PATENT DOCUMENTS

| | | |
|---|---|---|
| 3,899,579 A | 8/1975 | Anderson |
| 4,339,428 A | 7/1982 | Tencza |

(Continued)

FOREIGN PATENT DOCUMENTS

| | | |
|---|---|---|
| WO | WO 00/15167 | 3/2000 |
| WO | WO 2004/013408 | 2/2004 |

OTHER PUBLICATIONS

Moustakakis et al. (Clin Kidney J. 2012; 5:552-555).*

(Continued)

*Primary Examiner* — Ernst V Arnold

(57) ABSTRACT

A composition including a hydrate form of magnesium oxide, denoted as $MgO \cdot (H_2O)_n$, at a concentration ranging from 1 to 100 weight percent (wt %), where n is any value from 0.1 to 2. The composition may further include MgO at a concentration ranging from 0 to 99 wt %; or $Mg(OH)_2$, at a concentration ranging from 0 to 99 wt %; or $Mg(OH)_2$ at a concentration ranging from 0 to 99 wt %, and MgO, at a concentration ranging from 0 to 99 wt %.

13 Claims, 4 Drawing Sheets

Related U.S. Application Data

(60) Provisional application No. 61/826,736, filed on May 23, 2013.

(51) Int. Cl.
*A61K 31/675* (2006.01)
*A61K 45/06* (2006.01)

(56) References Cited

U.S. PATENT DOCUMENTS

| | | | |
|---|---|---|---|
| 7,994,217 B2* | 8/2011 | Nidamarty | A61K 31/198 424/630 |
| 2003/0139492 A1 | 7/2003 | Abu-Isa | |
| 2003/0157195 A1 | 8/2003 | Bartels | |
| 2005/0037070 A1 | 2/2005 | Hall et al. | |
| 2010/0260852 A1 | 10/2010 | Katsuki et al. | |
| 2010/0278913 A1 | 11/2010 | Sancilio et al. | |
| 2014/0348952 A1 | 11/2014 | Primor | |

OTHER PUBLICATIONS

Magnesium Hydroxide Safety Data Sheet 2014; 6 pages.*
Lu et al. (Abstract of: Clin Pharmacokinet. 2000;38(4):305-14) 2 pages.*
Omu et al. (Med Princ Pract. 2008;17:227-232).*
Official Action dated Jul. 9, 2015 From the U.S. Patent and Trademark Office Re. U.S. Appl. No. 14/194,833.
Official Action dated Jan. 11, 2016 From the U.S. Patent and Trademark Office Re. U.S. Appl. No. 14/194,833.
Restriction Official Action dated Apr. 21, 2015 From the U.S. Patent and Trademark Office Re. U.S. Appl. No. 14/194,833.
Ahdjoudi et al. "Adsorption of H2O on Metal Oxides: A Periodic Ab-Inition Investigation", Surface Science, 402-404: 104-109, May 15, 1998.
Alaimo et al. "Dietary Intake of Vitamins, Minerals, and Fiber of Persons Ages 2 Months and Over in the United States: Third National Health and Nutrition Examination Survey, Phase 1, 1988-91", National Center for Health Statistics, Centers for Disease Control and Prevention, NCHS, Advance Data, 258: 1-28, Nov. 14, 1994.
Altura et al. "Comparative Effects of a Mg-Enriched Diet and Different Orally Administered Magnesium Oxide Preparations on Ionized Mg, Mg Metabolism and Electrolytes in Serum of Human Volunteers", Journal of the American College of Nutrition, 13(5): 447-454, Oct. 1, 1994.
Aphane "The Hydration of Magnesium Oxide With Different Reactivities by Water and Magnesium Acetate", Thesis Submittes in Fulfillment of the Requirements for the Degree of Master of Science in the Subject Chemistry at the University of South Africa, XP055127389, p. 1-144, Mar. 2007.
Aranovich et al. "H2O Activity in Concentrated NaCl Solutions at High Pressures and Temperatures Measured by the Brucite-Periclase Equilibrium", Contributions to Mineralogy and Petrology, 125(2-3): 200-212, Oct. 1, 1996.
Ball et al. "The Dehydration of Brucite", Mineralogical Magazine, 32(253): 754-766, Jun. 1961.
Barnes et al. "Ideality and Ionization in Hydrothermal Fluids: The System MgO—H2O—NaOH", American Journal of Science, 261(2): 129-150, Feb. 1963.
Bothara "Inorganic Pharmaceutical Chemistry", Pragati Books, p. 9-7, 9-13, 9-20, Oct. 7, 2008.
Coudray et al. "Study of Magnesium Bioavailability From Ten Organic and Inorganic Mg Salts in Mg-Depleted Rats Using a Stable Isotope Approach", Magnesium Research, 18(4): 215-223, Dec. 2005.
Fine et al. "Intestinal Absorption of Magnesium From Food and Supplements", The Journal of Clinical Investigation, 88(2): 396-402, Aug. 1991.
Fingl et al. "Introduction: General Principles", The Pharmacological Basis of Therapeutics, Section I(Chap.1): 1-46, 1975.
Firoz et al. "Bioavailability of US Commercial Magnesium Preparations", Magnesium Research, 14(4): 257-262, Dec. 2001.
Irving et al. "Paleomagnetism of the Harp Lake Complex and Associated Rocks", Canadian Journal of Earth Sciences, 14(6): 1187-1201, Jun. 1977.
Johnson et al. "Brucite [Mg(OH)2] Dehydration and the Molar Volume of H2O to 15 GPa", American Mineralogist, 78(3-4): 271-284, Apr. 1, 1993.
Jost et al. "The Role of Reactivity in Syntheses and the Properties of Magnesium Oxide", Solid State Ionics, 101-103(1): 221-228, Nov. 30, 1997.
Kanzaki "Dehydration of Brucite (Mg(HO)2) at High Pressures Detected by Differential Thermal Analysis", Geophysical Research Letters, 18(12): 2189-2192, Dec. 1991.
Leinenweber et al. "Unquenchable High-Pressure Perovskite Polymorphs of MnSnO3 and FeTiO3", Physics and Chemistry of Minerals, 18(4): 244-250, Dec. 1, 1991.
Lindberg et al. "Magnesium Bioavailability From Magnesium Citrate and Magnesium Oxide", Journal of the American College of Nutrition, 9(1): 48-55, Feb. 1, 1990.
Liu et al. "Solvation of Magnesium Oxide Clusters With Water in Direct Laser Vaporization", International Journal of Mass Spectrometry and Ion Processes, 171(1): L7-L11, Dec. 31, 1997.
L'vov et al. "Mechanism of Thermal Decomposition of Magnesium Hydroxide", Thermochimica Acta, 315(2): 135-143, May 18, 1998.
Merck "Administration and Kinetics of Drugs", The Merck Manual Home Health Handbook, 3rd Ed., Chap.10: 1-8, 2009.
Merck "Magnesium Citrate", The Merck Index: An Encyclopedia of Chemicals, Drugs, and Biologicals, 11th Ed., p. 892, 1989.
Metabolics "The Definitive Guide to Magnesium & Magnesium Supplements", Metabolics.com, 8 P., Apr. 10, 2013.
Meyer et al. "Some Observations in the System MgO—H2O", American Journal of Science, 260(9): 707-717, Nov. 1962.
Muehlbauer et al. "Magnesium-L-Aspartate-HCl and Magnesium-Oxide: Bioavailability in Healthy Volunteers", European Journal of Clinical Pharmacology, 40(4): 437-438, Apr. 1991.
Ross et al. "A Case of Hypomagnesaemia Due to Malabsorption, Unrepsonsive to Oral Administration of Magnesium Glycerophosphate, But Responsive to Oral Magnesium Oxide Supplementation", Gut, 48(6): 857-858, Jun. 1, 2001.
Saris et al. "Magnesium. An Update on Physiological, Clinical and Analytical Aspects", Clinica Chimica Acta, 294(1-2): 1-26, Apr. 30, 2000.
Schramke et al. "Experimental Determination of the Brucite=Periclase+Water Equilibrium With a New Volumetric Technique", American Mineralogist, 67(3-4): 269-276, Apr. 1982.
Schuette et al. "Bioavailability of Magnesium Diglycinate Vs. Magnesium Oxide in Patients With Ileal Resection", Journal of Parenteral and Enteral Nutrition, 18(5): 430-435, Sep. 1, 1994.
Schuette et al. "Dysprosium as a Nonabsorbable Marker for Studies of Mineral Absorption With Stable Isotope Tracers in Human Subjects", Journal of the American College of Nutrition, 12(3): 307-315, Jun. 1993.
Seelig "Cardiovascular Consequences of Magnesium Deficiency and Loss: Pathogenesis, Prevalence and Manifestations—Magnesium and Chloride Loss in Refractory Potassium Repletion", The American Journal of Cardiology, 63(14): 4G-21G, Apr. 18, 1989.
Seelig "The Requirement of Magnesium by the Normal Adult", American Journal of Clinical Nutrition, 14(6): 342-390, Jun. 1964.
Seelig et al. "The Magnesium Factor", Penguin Books, Aug. 2003.
Shechter "Magnesium and Cardiovascular System", Magnesium Research, 23(2): 1-13, Jun. 2010.
Shechter et al. "Effects of Oral Magnsium Therapy on Exercise Tolerance, Exercise-Induced Chest Pain, and Quality of Life in Patients With Coronary Artery Disease", American Journal of Cardiology, 91(5): 517-521, Mar. 1, 2003.
Thermo Fischer Scientific "Magnesium Hydroxide", Acros Organics, Thermo Fischer Scientific, Safety Data Sheet, p. 1-6, Sep. 17, 2014.
Troy et al. "Antacid Mixtures", Remington: The Science and Practice of Pharmacy, Chap.66: 1297, 2006.

(56) References Cited

OTHER PUBLICATIONS

Xin et al. "Effect of Reactivity Rate and Particle Size of Magnesium Oxide on Magnesium Availability, Acid-Base Balance, Mineral Metabolism, and Milking Performance of Dairy Cows", Journal of Dairy Science, 72(2): 462-470, Feb. 28, 1989.
Yamaoka et al. "Phase Equilibrium in the System MgO—H2O at High Temperatures and Very High Pressures", Journal of the American Ceramic Society, 53(4): 179-181, Apr. 1, 1970.
Doyle et al. "Magnesium Sulphate for Women at Risk of Preterm Birth for Neuroprotection of the Fetus (Review)", Cochrane Database of Systemic Reviews, 1(Art.No. CD004661): 1-145, Published Online Jan. 21, 2009.
Drugs.com "Magnesium Sulfate", Drugs.com, Description Sheet, 9 P., Review Date Jul. 5, 2017.
Shechter et al. "Comparison of Magnesium Status Using X-Ray Dispersion Analysis Following Magnesium Oxide and Magnesium Citrate Treatment of Healthy Subjects", Magnesium Research, 25(1): 28-39, Mar. 1, 2012.
Communication Pursuant to Article 94(3) EPC dated Sep. 22, 2017 From the European Patent Office Re. Application No. 14151507.6. (1 Page).

\* cited by examiner

MAGNESIUM-CONTAINING PRODUCTS AND USES THEREOF

RELATED APPLICATIONS

This application is a division of U.S. patent application Ser. No. 14/194,833 filed on Mar. 3, 2014, which claims the benefit of priority of U.S. Provisional Patent Application No. 61/826,736 filed on May 23, 2013.

The contents of the above applications are all incorporated by reference as if fully set forth herein in their entirety.

FIELD AND BACKGROUND OF THE INVENTION

The present invention relates to the field of supplemental products, and more particularly, but not exclusively, to novel magnesium (Mg)-containing products, method of preparing same and uses thereof as magnesium supplements with enhanced bioavailability in humans.

Magnesium is a natural element widely diffused in living organisms, especially in mammals, wherein the largest concentration thereof occurs in bones. The participation of magnesium ions in the human body has been established in most reactions of carbohydrates, lipids, nucleic acids, and in protein metabolism.

Magnesium is the fourth most abundant cation in the human body and plays an essential physiological role in many of its functions. This role is achieved through two important properties of magnesium; the ability to form chelates with important intracellular anionic-ligands, especially ATP, and its ability to compete with calcium for binding sites on proteins and membranes. By competing with calcium for membrane binding sites and by stimulating calcium sequestration by sarcoplasmic reticulum, magnesium helps to maintain a low resting intracellular free calcium ion concentration which is important in many cellular functions. The electrical properties of membranes and their permeability characteristics are also affected by magnesium.

Magnesium, being a normal component of the blood plasma and a calcium antagonist, takes part in the muscle contraction mechanism and is vital for the action of a number of enzymes. Magnesium balance in organism is tightly controlled by the dynamic action of intestinal absorption, exchange with bone, and renal excretion.

Magnesium is estimated to be distributed in the body as follows: 53% in the bone, 27% in muscle, 19% in soft tissue, 0.5% in erythrocytes, and 0.3% in serum. Of the serum magnesium, 33% is protein-bound, 12% is complexed to anions, and 55% is in the free ionized form. Total magnesium stores in the body average 24 grams (2000 mEq) elemental magnesium, and a normal serum concentration is in the range of 1.7-2.5 mg/dL (1.4-2.1 mEq/L).

Mg is transported to the different body compartments in the blood plasma, either as free ionized Mg, bound to relatively small (ultrafiltrable) complexes (e.g. citrate) or bound to proteins (albumin, globulin), which are not ultrafiltrable. The concentration of Mg in serum is kept relatively constant. However, it has been shown that there is no apparent correlation between serum and tissue magnesium levels, with exception of bone and interstitial fluid, and therefore serum magnesium measurements do not accurately reflect the amount of magnesium present in the body.

Magnesium excretion is the main pathway for regulating Mg levels in the blood. About 70-80% of plasma Mg (ultrafiltrable Mg) is filtered in the kidney. Of this ultrafiltrable Magnesium, 20-25% is reabsorbed by the proximal tube, 50-60% in the loop of Henle, and 5% in terminal segments, while the remainder (5-20%) is excreted in the urine. Magnesium is excreted from the gastrointestinal tract at a rate of approximately 2 mEq/day. Further significant loss of magnesium can be caused by drugs such as amphotericin B, cisplatin, digoxin, pentamidine, gentamicin, and loop diuretics via renal wasting of magnesium in the renal tubule.

The daily magnesium requirement for humans ranges from 5 to 10 mg/per kg body weight, and is normally supplied through the food, particularly vegetables. However, as the magnesium food content in the Western world is consistently reducing, magnesium deficiency, or hypomagnesaemia, has become a prevalent condition. While the average daily intake of magnesium at the beginning of the 20th century was 410 mg, today it is only 200-300 mg. This is attributed to the processed nature of the contemporary diet (Seelig and Rosanoff, 2003).

The current daily Recommended Dietary Allowances for magnesium is 420 mg/day for males and 320 mg/day for females above 31 years, with an additional 300 mg/day during pregnancy or physical growth. Surveys show that a substantial number of adults in the United States fail to consume recommended daily amounts of magnesium. Dietary surveys show that the average intake in many western countries is less than the RDA (Saris et al., 2000). In a population-based study of 30-year old Israelis, about 60% had magnesium deficiency (Shechter, 2010; Seelig, 1964; Centers for Disease Control and Prevention, 1994).

Magnesium homeostasis is essential for many intracellular processes and depends on the balance of intestinal absorption and renal excretion. Hypomagnesaemia may arise from various disorders. A magnesium deficiency, or hypomagnesaemia, is common in hospitalized patients, especially in the elderly with coronary artery disease (CAD) and/or those with chronic heart failure. Hypomagnesemia is often associated with increased incidence of diabetes mellitus, metabolic syndrome, mortality rate from coronary artery disease (CAD) and all cause.

Hypomagnesaemia is also associated to abnormal muscle excitability as well as convulsions, to psychiatric disturbances, and to calcium and/or potassium abnormalities.

Diminished content of magnesium in blood serum contributes to the development of hypercalcemia, spasm of arterioles, and the occurrence of muscular convulsions and trophic disorders and thus plays an essential role in the pathogenesis of changes of the blood flow and trophic disorders.

Magnesium deficiency can occur in babies from birth, when the mother was already depleted of her own magnesium reserves, or when the baby is poorly supplied with magnesium, and/or undergoes high magnesium losses from his or her organism. When encountered in an adolescent, adult or aged person, a magnesium deficiency can be also ascribed to generally stressing conditions, chronic intoxication or disease, to malabsorption, to alcohol or drugs abuse, as well as to hormone pathologies that cause magnesium losses for long time periods. A magnesium deficiency referable to a poor supply can be also due to, e.g., growth, pregnancy, breast feeding, anorexia, vomiting, overload of calcium, of vitamin D, of phosphorus, of alkalizing products, or excessive intake of alimentary fiber, low calorie diets, alcoholism, etc. A magnesium deficiency referable to defects in magnesium metabolism can be due to, e.g., stress or neurosis, nervous disorders or endocrine-metabolic disorders.

In addition to conditions or disorders caused by magnesium deficiency, magnesium supplements have been shown to have a therapeutic effect in many other conditions or disorders, including, for example, constipation, preeclampsia, leg cramps, cerebral palsy, depression, asthma, cardiovascular diseases, ischemic heart disease, cardiac arrhythmias, hypertension, pregnancy-induced hypertension, strokes, cerebrovascular diseases, osteoporosis, alcohol withdrawal, preterm labor, fatigue, renal stones, kidney, stones, headache, migraine, altitude sickness, premenstrual syndrome, fibromyalgia, muscle weakness, insulin resistance, bronchospasms, hyperlipidemia, mitral valve prolapse, neonatal encephalopathy, and diabetes mellitus.

Magnesium supplementation has been shown to improve myocardial metabolism, to inhibit calcium accumulation and myocardial cell death; to improve vascular tone, peripheral vascular resistance, and afterload and cardiac output, to reduce cardiac arrhythmias and to improve lipid metabolism.

A magnesium deficiency or excess in an organism cannot be quantified as an absolute value, as the magnesium level in the blood is not related with the presence thereof in the deposit sites, as discussed hereinabove. Generally speaking, the means for detecting the magnesium body contents include the detection of blood levels of magnesium, in the patient's plasma or in the serum (whose anomalies generally indicate a disorder in magnesium metabolism and are, normally, the starting point for a set of further specific tests); the detection of magnesium levels in the urine (which gives a measure of the elimination of magnesium via urine, and is normally associated with protein intake, being the Mg/urea ratio in the urine quite constant); the detection of magnesium levels in the spinal fluid; the detection of erythrocytic magnesium (which shows the amount of Mg contained in the bone marrow when erythropoiesis occurs and allows, therefore, an indirect medullary exploration as concerns magnesium); the detection of lymphocytic magnesium; nuclear magnetic resonance with $^{25}$Mg (which evidences any modifications in the subcellular distribution of magnesium and in the different chemical-physical structures); and, the detection of magnesium contents in the patient's bones, muscles or any other tissue or organ of interest.

In view of the widespread recognition of the involvement of magnesium in a variety of disorders and conditions, and the increased need in magnesium supplementation, magnesium-containing products became a highly recommended standard of care.

Herein throughout, in the context of magnesium-containing products, magnesium supplements, magnesium formulations and/or magnesium therapy, the term "magnesium" refers to $Mg^{+2}$ ions, either in a form of free ions in a salt or in a form of a complex.

Currently available Mg-containing products that are aimed at magnesium supplementation are formulated mainly for intravenous or oral administration. An oral route of administration is more convenient, and usually the safest and least expensive, whereas intravenous administration must be performed by a health care worker, and has additionally sparked some concern as to possible elevation of serum levels of magnesium to the toxic range. However, the decreased absorption associated with oral administration poses a significant obstacle in administration (The Merck Manual Home Health Handbook, 2009, Chapter 10).

When administered orally, magnesium was shown to be absorbed primarily in the small intestine in the ileum and jejunum, and the degree of absorption has been shown to depend upon the amount of magnesium already present in the diet and the amount of magnesium administered. As indicated by radioactive $^{28}$Mg studies, absorption begins approximately 1 hour after oral intake, plateaus after 2-5 hours, and then declines. After 6 hours Mg absorption is about 80% complete.

Studies have shown that inorganic magnesium salts may have a bioavailability equivalent to organic magnesium salts, depending on the preparation (Firoz and Graber, 2001). It has further been shown that magnesium salts are converted to magnesium chloride in the stomach (Seelig, 1989). Non-absorbed magnesium (not uptaken by cells), due to high oral loads or inefficient absorption, can cause a number of side effects, including diarrhea, heartburn, nausea, and upset stomach.

Currently available magnesium-containing products for oral administration include, for example, magnesium oxide, magnesium carbonate, magnesium hydroxide, magnesium citrate, magnesium lactate, magnesium gluconate, magnesium chloride, magnesium aspartate, magnesium caprilate, magnesium pidulate and magnesium sulfate. Intravenously administered magnesium includes, for example, magnesium sulfate. It is to be noted that oral administration of acidic magnesium salts, which generate relatively strong acids in the stomach (e.g., magnesium chloride and magnesium sulfate) is limited by the tolerable amount that can be taken, since it can cause non-tolerable acidity in the stomach.

In order for Mg-containing product to be therapeutically effective, it should be able to release a form of ionized magnesium which can be uptaken into the cells to perform its essential functions. As noted hereinabove, the level of serum magnesium does not necessarily correlate to levels of cellular magnesium, and therefore the identification of an effective Mg supplementation should be determined by its cellular uptake. Since magnesium has no specific target tissue, its bioavailability cannot be assessed directly. Therefore, other parameters such as retention, absorption, and urinary excretion are used as a measure for magnesium oral bioavailability. Intravenously administered magnesium is considered to be 100% bioavailable.

Several independent studies have been performed in order to evaluate the absorption of different forms of orally administered magnesium supplements. However, conflicting data regarding the absorption rates of magnesium as a function of the supplement formulation are found in the art.

Magnesium oxide capsules were better absorbed than magnesium-L-aspartate HCL tablets as measured by urinary excretion of magnesium, while plasma magnesium levels remained unchanged (Muhlbauer et al., 1991). Magnesium oxide preparation improved serum magnesium in those with low basal serum levels, but not in those with normal/high serum levels, in a study of magnesium absorption in subjects given magnesium-enriched diets followed by either magnesium oxide or magnesium phosphate plus oxide (Altura et al., 1994). The superiority of magnesium oxide absorption over magnesium glycerophosphate was observed in patients with shortened small bowel-induced malabsorption (Ross et al., 2001). Another study showed that MgO was significantly less well absorbed than a comparable amount of Mg citrate as measured by urinary excretion four hours post load (Lindberg et al., 1990). In another study, MgO showed increased urinary excretion as compared with a comparable amount of $MgCl_2$, Mg lactate, and Mg aspartate (Firoz and Graber, 2001). However, in other studies (Schuette et al., 1993 and Schuette et al., 1994) there was no significant difference observed between uptakes of MgO as compared with Mg diglycinate.

Yet another study compared the delivery of MgAc in gelatin capsules to magnesium chloride in enteric-coated capsules. The lower absorption of the enteric-coated capsules was attributed to the 3-5 hour exposure necessary to fully release the capsule's contents, which reduced the small bowel absorptive area to which the Mg is exposed (Fine et al., 1991).

One study on livestock reported that the particle size of the MgO affects its absorption, a phenomenon which could explain the conflicting results about MgO absorption (Xin et al., 1989).

Several means have been devised to overcome the poor absorption of MgO. Efforts were made to utilize small MgO particles, yet, are hindered by the tendency of the magnesium oxide particles to strongly agglomerate. Resulting agglomerates require a high shear force for re-pulverization at the time of incorporation into absorbable preparations, and thus adversely affect other ingredients in any planned preparations.

The present inventor discovered that a special form of magnesium oxide is useful to overcome not only the problems of agglomeration but also provide enhancing bioavailability of magnesium.

Magnesium oxide, also known as the mineral periclase, can be formed by calcination at high temperatures from magnesium carbonate (Liu et al, 1997), by thermal decomposition of magnesium chloride (Jost et al. 1997), or by dehydration of magnesium hydroxide.

The dehydration of magnesium hydroxide (also referred to in the art as brucite), so as to form magnesium oxide and water has been studied extensively in the art (Meyer and Yang, 1962; Barnes and Ernst, 1963; Aranovich and Newton, 1996; L'vov et al., 1998).

It has been shown that this reaction occurs under defined pressure-temperature conditions (see, for example, Schramke et al., 1982; and corresponding Background Art FIG. 1, further discussed hereinbelow).

Schramke et al. (1982) used a method of measuring volume changes of encapsulated samples during the experimentation of the brucite-periclase equilibrium, in order to avoid quenching problems. The results agree with data obtained from thermochemical techniques, as reflected in Background Art FIG. 1. Notably, the curve for the dehydration of brucite and the curve for the hydration of periclase do not demonstrate the same values.

Meyer and Yang (1962) reported that the dehydration curve obtained by temperature quenching and the hydration curve obtained by pressure quenching are about 40° C. apart at elevated pressures. They proposed that the difference between the 2 curves is due to the formation of an intermediate phase, corresponding to a distorted periclase which rapidly rehydrates during quenching.

Barnes and Ernst (1963) investigated the brucite periclase equilibrium at pressures up to 2 kbar using cold-seal hydrothermal pressure vessels with water as the pressure medium. In their study, they developed two procedures to avoid confusing the effects of a back reaction during the quench.

Johnson and Walker (1993) determined accurately the brucite dehydration equilibrium from 1 to 15 GPa. The approach adopted was a combination of differential thermal analysis (DTA) and quenching experiments. The quenching experiments are more reliably interpreted than in other studies because thermal gradients cause diffusive migration of periclase and $H_2O$ to different regions of the experimental charge. This separation facilitates quenching of periclase in experiments outside the brucite stability field. In the quenching experiments, samples were brought to the desired pressure and temperature, held there for 30 minutes, and then quenched by shutting off furnace power. Background Art FIG. 2 presents an experimentally determined phase diagram for the dehydration of brucite determined by differential thermal analysis (circles), and quenching techniques (squares), and additionally presenting an interface in which magnesium hydroxide and magnesium oxide were stable (open squares), and temperatures at which both brucite and periclase were stable (half-shaded squares)).

Additional experiments and data from Yamaoka et al., 1970; Irving et al., 1977; Kanzaki, 1991; and Leinenweber et al., 1991, have shown similar results (see, Johnson and Walker, 1993).

Ball and Taylor (1961) have studied the dehydration process of brucite to periclase using X-rays measurements and found that this process involves a formation of spinel-like intermediate, which gave "extra" reflections, and was obtained when a pure brucite crystal was heated in air to 800° C. for 45 minutes. Ball and Taylor have suggested that during the formation of periclase, donor and acceptor regions are developed in the brucite crystal, and that the reaction proceeds not by loss of hydroxyl ions, but rather by gain of cations and loss of protons. The formed cations migrate into the donor regions, and their hydroxyl ions provide all the oxygen for the water that is formed, as shown in Background Art FIG. 3. Ball and Taylor have assumed that the formed spinel-like intermediate has a molecular formula of $Mg_3O_4H_2$, which corresponds to a molecule of water to which 3 molecules of MgO are complexed to form a kind of hydrate.

Ahdjoudj and Minot (1998) describe ab initio periodic Hartree-Fock calculations of water molecules on MgO and teach that the water molecule does not dissociate on MgO and is adsorbed parallel to the surface, with the main interaction concerning the Mg from the surface and the p-orbital electron pair of the water.

Means for providing magnesium to the human body as a supplement have been proposed in the art. Despite the ability of existing magnesium supplements to increase magnesium levels to some extent, there is a considerable need for an improved magnesium-containing composition, able to enhance the uptake of magnesium in humans. The present invention satisfies these needs due to enhanced bioavailability of a specific hydrate form of magnesium oxide, and provides manifestative health benefits as well.

SUMMARY OF THE INVENTION

The present invention, in some embodiments thereof, relates to the field of supplemental products, and more particularly, but not exclusively, to novel magnesium (Mg)-containing products, processes of preparing same and uses thereof as magnesium supplements to provide enhanced bioavailability of magnesium in humans. In particular, the present invention relates to a composition including a hydrate form of magnesium oxide, denoted as $MgO.(H_2O)n$, at a concentration ranging from 1 to 100 weight percent (wt %), where n is any value from 0.1 to 2. The inventor discovered that a special form of magnesium oxide is useful to overcome not only the problems of agglomeration but also to provide enhanced bioavailability of magnesium.

According to preferred embodiments of the present invention, there is provided a pharmaceutical composition and a method for preventing magnesium deficiency in the humans and non-humans, the method comprising orally administering a therapeutically effective amount of the pharmaceutical composition which comprises an effective amount of a special hydrate form of magnesium oxide, which is denoted herein as magnesium oxide hydrate MgO.(H$_2$O)n, extracted from the Dead Sea (Israel).

The present invention also relates to the use of a magnesium oxide hydrate of the form MgO.(H$_2$0)n, where n=0.1 to 2, in the manufacture of a magnesium supplement.

According to some embodiments of the invention, the magnesium oxide-type composition is selected from the group consisting of MgO, Mg(OH)$_2$ and MgO.(H$_2$O)n, wherein n is any value from 0.1 to 2.

According to other embodiments of the invention, the therapeutically effective amount is equivalent to an amount of elemental magnesium that ranges from 50 mg/day to 2000 mg/day.

According to some embodiments of the invention, the pharmaceutical composition is a unit dosage form composition for oral administering and is formulated as a sachets, pills, caplets, capsules, tablets, chewing gums and any other chewable composition, dragee-cores or discrete (e.g., separately packaged) units of powder, granules, or suspensions or solutions in water or non-aqueous media.

Further provided in the present invention, there is a pharmaceutical composition characterized as capable of generating free magnesium ions from at least 50% of its magnesium content under physiological conditions of a human stomach during a time period that is equivalent to a retention time of the composition in a human stomach.

In other embodiments, the invention provides a magnesium oxide-type composition and a method of administering of magnesium supplementation to a subject is described herein. Such a method may comprise oral administering to the subject at least one unit dosage providing efficient amount of a magnesium oxide-type composition sufficient to enhance bioavailability of magnesium [Mg$^{2+}$]$_i$.

In some embodiments, the present invention provides a method of determining a concentration of magnesium to produce a physiological effect. In some embodiments, the concentration of magnesium is measured after fasting in biological fluids selected from blood, serum and plasma. In related embodiments, concentration of intracellular magnesium [Mg$^{2+}$]$_i$ is measured with in sublingual epithelial cells through X-ray dispersion.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. The drawings are illustrative and are not necessarily drawn to scale.

In the drawings:

FIG. 5A shows the experimental setup, with a MgO/MgO.(H$_2$O) n-containing sample at the center flask. FIGS. 5B and 5C show the magnesium citrate-containing samples.

DETAILED DESCRIPTION OF THE INVENTION

Before explaining at least one embodiment of the invention in detail, it is to be understood that the invention is not necessarily limited in its application to the details set forth in the following description or exemplified by the Examples. The invention is capable of various alternatives to the embodiments or of being practiced or carried out in various ways.

In a search for an effective magnesium source that can be efficiently used orally as a magnesium-containing supplement, it was uncovered that magnesium oxide salts, e.g., from the Dead Sea (Israel), exhibit improved pharmacological effects, particularly in terms of cellular uptake (intracellular absorption) and, thus, exhibit a superior performance, as compared to other currently available Mg-containing supplements.

More particularly, it was uncovered that products containing unique magnesium oxide salts from the Dead Sea exhibit enhanced dissolution and consequently enhanced generation of Mg$^{2+}$ ions, under acidic conditions. In parallel, it was discovered that oral administration of products containing these specific magnesium oxide salts results in elevated levels of intracellular magnesium [Mg$^{2+}$]$_i$, which were not observed when other magnesium-containing products were used.

Herein throughout, the expression "Mg-containing product" encompasses any composition, formulation, unit dosage form, and the like, which comprises a magnesium form that is capable of releasing Mg$^{+2}$ ions.

In the broadest scope of the invention, the magnesium-containing products disclosed herein comprise a hydrate form of magnesium oxide, preferably from the Dead Sea. Without being bound to theory, t was hypothesized by the inventor, with reference to magnesium salts from the Dead Sea, that the extreme climatic conditions of this region have an impact on the formation of such a unique and specific form of Magnesium oxide which exhibits X-ray powder patterns characteristic of a hydrate form of MgO (see, Ball and Taylor, 1961, supra). This hydrate form of magnesium oxide is a fine, slightly gray powder. According to preferred embodiments, this magnesium oxide hydrate is taken, as is, from the Dead Sea and used in an unprocessed form. While such a hydrate compound can be manufactured in synthetic form for use in the pharmaceutical compositions of the present invention, it is much more costly to prepare in this fashion.

Figure 1:
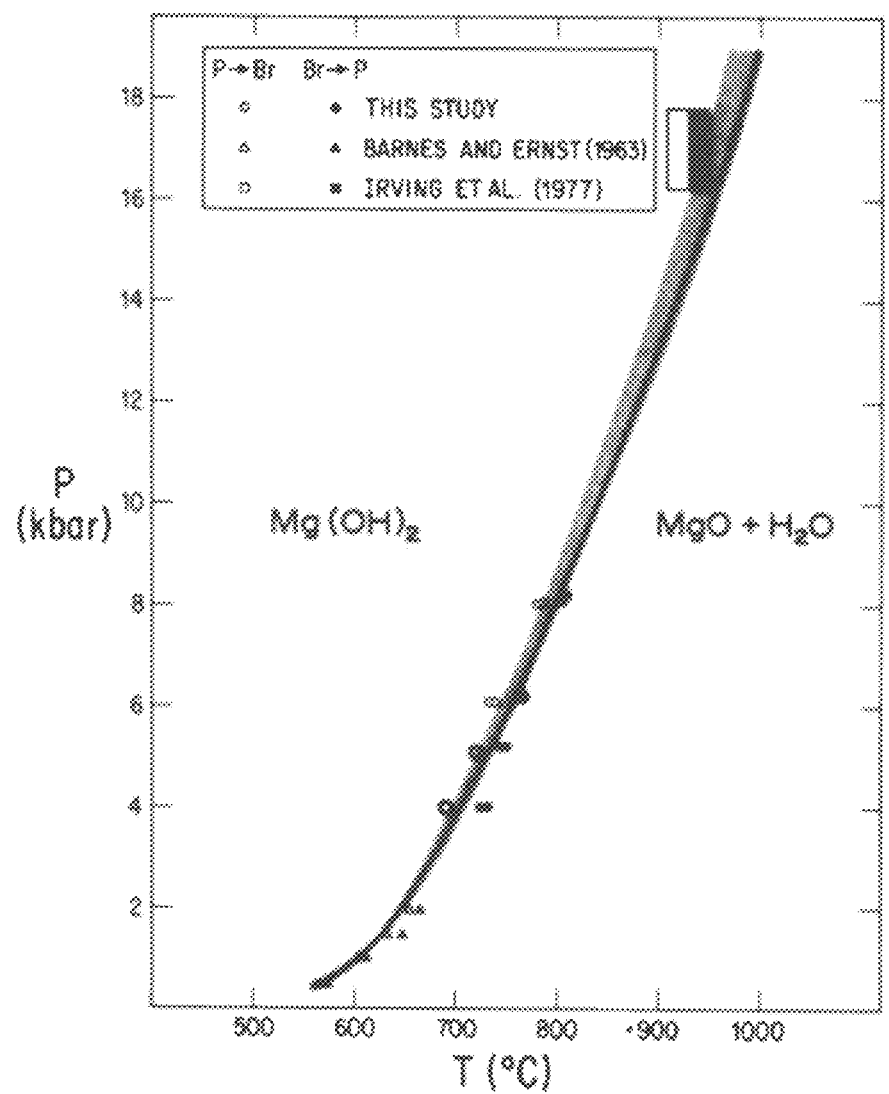
FIG. 1 (Background Art, taken from Schramke et al. (1982; supra)) presents an experimentally determined phase diagram for the dehydration of brucite, wherein filled figures represent the transition from brucite to periclase, and empty figures represent the transition from periclase to brucite, and wherein circles represent data determined by Schramke et al. (1982; supra, denoted "this study"), triangles represent data determined by Barnes and Ernst (1963; supra) and squares represent data determined by Irving et al. (1977; supra). The shaded area represents the extrapolation from the end-points of the 8.1 kbar bracket of this study. The solid line is the extrapolated equilibrium curve from the starting-point at 8.0 kbar and 800° C.
Figure 2:
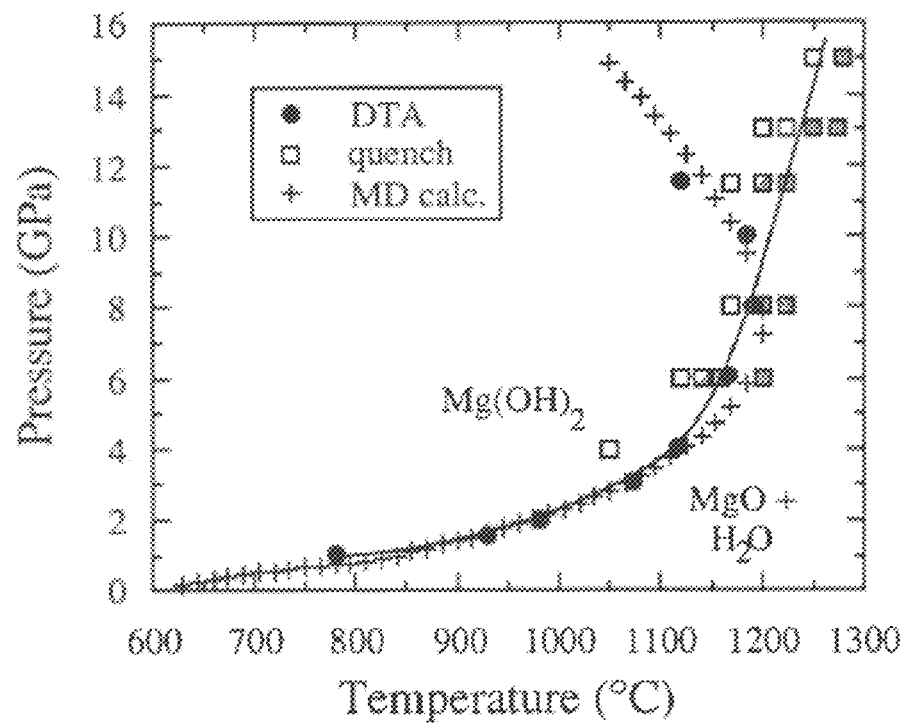
FIG. 2 (Background Art taken from Johnson and Walker, 1993 (supra)) presents an experimentally determined phase diagram for the dehydration of brucite wherein circles represent data determined by differential thermal analysis, squares represent data determined using quenching techniques, open squares indicate an interface in which magnesium hydroxide and magnesium oxide were stable, half-stippled squares represent temperatures at which both brucite and periclase were stable, and the plus signs are a theoretical phase boundary calculated using molecular dynamics.
Figure 3:
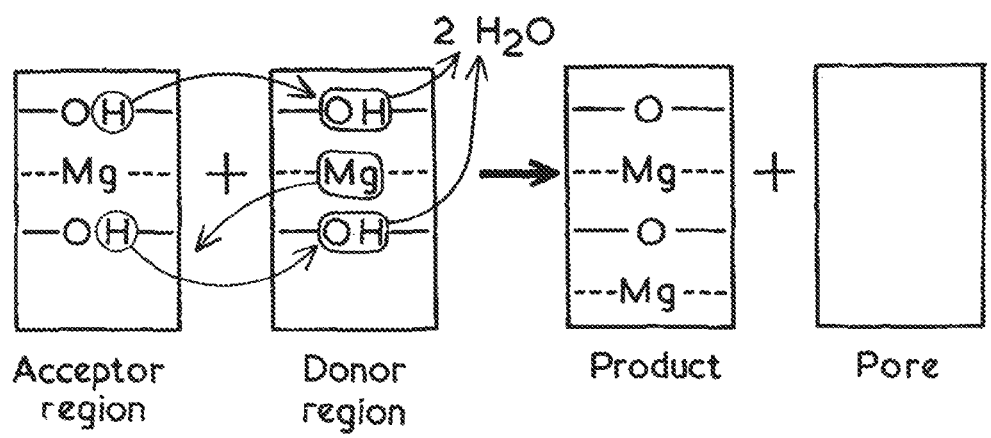
FIG. 3 (Background Art taken from Ball and Taylor (1961; supra)) presents a schematic representation of the acceptor and donor regions, showing the migration of ions in opposite directions and the expulsion of water from the donor region, during the transformation of brucite to periclase.

According to the studies discussed in the Background section hereinabove and summarized in FIGS. 1 and 2, a hydrate form of magnesium oxide could be obtained by those skilled in the art. The FIGS. 1 and 2 demonstrate that the brucite ⇆ periclase transition involves three possible phases: magnesium oxide (MgO; periclase), water, and magnesium hydroxide ($Mg(OH)_2$; brucite). The curve expresses the conditions at which the magnesium hydroxide releases the water ($H_2O$) molecule, and thus represents the point where a hydrate form of magnesium oxide monohydrate may be formed (prior to the formation of separate phases of MgO and water).

Thus, according to an aspect of some embodiments of the present invention there is provided a composition which comprises:

MgO, at a concentration ranging from 0 to 99 weight percent (wt %);

$Mg(OH)_2$, at a concentration ranging from 0 to 99 wt %; and $MgO.(H_2O)n$, at a concentration ranging from 1 to 100 wt %, wherein n is any value from 0.1 to 2.

The disclosed composition thus comprises a hydrate form of magnesium oxide, which is denoted herein as $MgO.(H_2O)$n. The phrases "hydrate form of magnesium oxide" and "a magnesium oxide hydrate", and any other diversion of these phrases, are used herein interchangeably with respect to $MgO.(H_2O)n$.

$MgO.(H_2O)n$ encompasses a form of magnesium oxide which is in a complex with water molecule or molecules, at the indicated stoichiometric ratio ($MgO:H_2O=1:n$).

Without being bound by any particular theory as to the specific nature of this complexation, one or more water molecules are assumed to be adsorbed to the surface of one or more magnesium oxide molecules via electrostatic forces.

Thus, for example, when n equals 1, $MgO.(H_2O)n$ is a monohydrate form of magnesium oxide, meaning that one molecule of MgO is complexed to one molecule of water, and, when taken as a crystal, means that each molecule of MgO in the crystal interacts with one water molecule.

When n equals 2, $MgO.(H_2O)n$ is a dihydrate form of magnesium oxide, meaning that one molecule of MgO is complexed to two molecules of water, and, when taken as a crystal, means that each molecule of MgO in the crystal interacts with two water molecules.

When n equals, for example, 1.5, $MgO.(H_2O)n$ is a hydrate form of magnesium oxide, in which 2 molecules of MgO are complexed to 3 molecules of water, and, when taken as a crystal, means that the MgO and water molecules in the crystal structure are arranged in a structure composed of clusters of 2 MgO molecules and 3 water molecules.

When n is lower than one, $MgO.(H_2O)n$ is a hydrate form of magnesium oxide in which several MgO molecules are complexed to one water molecule, and, when taken as a crystal, means that means that the MgO and water molecules in the crystal structure are arranged in a structure composed of clusters of several MgO molecules and a respective lower number of water molecules.

As non-limiting examples, when n is 0.66, it means that 2 water molecules are complexed to 3 MgO molecules and when n is 0.33, it means that one water molecule is complexed to 3 MgO molecules.

In some embodiments, n ranges from 0.3 to 1, and can be, for example, 0.3, 0.33, 0.4, 0.5, 0.66, 0.75, 0.8 or 1. However, n values of 1.2, 1.33, 1.5, 1.66, 1.75, 1.8, 2 are also contemplated.

Herein throughout, MgO is also referred to herein interchangeably as magnesium oxide or periclase, and refers to a non-hydrated form of magnesium oxide, unless otherwise indicated.

Herein throughout, $Mg(OH)_2$ is also referred to herein interchangeably as magnesium hydroxide, magnesium dihydroxide and brucite.

The composition disclosed herein comprises at least 1 weight percent (wt %) of $MgO.(H_2O)n$.

In some embodiments, the composition comprises $MgO.(H_2O)n$ at a concentration in the range of at least 10 wt % to at least 95 wt % of a total weight of the composition.

In some embodiments, the composition consists of $MgO.(H_2O)n$, such that its concentration is 100 wt % and the concentration of MgO and $Mg(OH)_2$ is 0.

In some embodiments, the composition comprises a mixture of $MgO.(H_2O)n$, at any of the concentrations described herein, and one or both of MgO and $Mg(OH)_2$.

In some embodiments, the composition comprises from 10 to 90 wt % one or both of MgO and $Mg(OH)_2$, and the balance is $MgO.(H_2O)n$.

In some embodiments, the composition comprises from 20-80 wt % one or both of MgO and $Mg(OH)_2$, and the balance is $MgO.(H_2O)n$.

In some embodiments, the composition comprises from 30-70 wt % one or both of MgO and $Mg(OH)_2$, and the balance is $MgO.(H_2O)n$.

In some embodiments, the composition comprises from 40-60 wt % one or both of MgO and $Mg(OH)_2$, and the balance is $MgO.(H_2O)n$.

In some embodiments, the composition comprises 50 wt % of one or both of MgO and $Mg(OH)_2$, and 50 wt % $MgO.(H_2O)n$.

In some embodiments, the composition is in a powder form, which comprises a plurality of particles.

In some embodiments, the particles have an average size that is from about 0.5 mm to about 1.5 mm.

In some embodiments, at least 50%, or at least 60%, or at least 70%, of the particles have a size of from about 0.2 mm to about 0.6 mm (30-60 mesh).

In some embodiments, the composition is characterized by a surface area of from about 30 $m^2$/gram to about 40 $m^2$/gram, or from about 32 $m^2$/gram to about 38 $m^2$/gram, or from about 34 $m^2$/gram to about 36 $m^2$/gram, or can be equal to about 35 $m^2$/gram. In some embodiments, the surface area is determined by BET measurements.

In some embodiments, the composition is a free-flowing powder, characterized by a bulk density lower than 1 gram/ml (e.g., of 0.90 gram/ml).

In particular embodiments of the invention, the composition further may comprise at least one additional ingredient selected from the group consisting of (a) water soluble vitamins, and (b) fat soluble vitamins.

According to an aspect of some embodiments, the composition comprises a therapeutic amount of Vitamin $B_6$.

In other embodiments of the present invention, the composition comprises therapeutic amounts of Vitamin E and Vitamin D.

Various processes known to those skilled in the art can be used to prepare the composition as described herein. Exemplary processes are described in Example 1 in the Examples section that follows.

The composition as described herein is characterized by improved pharmacological features and, thus, can be advantageously formulated into a pharmaceutical composition.

According to an aspect of some embodiments of the present invention, there is provided a pharmaceutical composition which comprises the composition as described herein.

As used herein, a "pharmaceutical composition" or "medicament" refers to a preparation of one or more of the compounds or compositions comprising two or more compounds as described herein, with other chemical components, such as pharmaceutically acceptable and suitable carriers and excipients.

The purpose of a pharmaceutical composition is to facilitate administration of a compound or a composition comprising two or more compounds, as described herein, to a subject.

The term "active ingredient" refers to a compound, or a composition comprising two or more compounds, as described herein, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered composition.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of active ingredients are well known in the art. Pharmaceutical compositions for use in accordance with the present invention thus may be formulated in a conventional manner, optionally, but not necessarily, using one or more pharmaceutically acceptable carriers comprising excipients and auxiliaries, which facilitate processing of the compounds or compositions into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl and Woodbury, 1975).

In some embodiments, the pharmaceutical composition is formulated for oral administration.

Compositions for oral administration include powders or granules, capsules or tablets, suspensions or solutions in water or non-aqueous media, sachets, pills, caplets. Thickeners, diluents, flavorings, dispersing aids, emulsifiers or binders may be desirable.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents. Such agents can be, for example, vitamins, hormones, preservatives, growth factors, anti-microbial agents, anti-inflammatory agents.

In some embodiments, the pharmaceutical composition is formulated as a unit dosage form for oral administration.

As used herein and in the art, the phrase "dosage form" describes a final physical form an active ingredient for consumption by a subject. The phrase "unit dosage form" describes physically discrete units, each unit containing a predetermined quantity of the active ingredient, herein the disclosed composition, calculated to produce the desired therapeutic effect, optionally in association with at least one pharmaceutically acceptable carrier, diluent, excipient, additional active or non-active agents or combination thereof, as described herein.

In some embodiments, the pharmaceutical composition disclosed herein is formulated, for example, as sachets, pills, caplets, capsules, tablets, chewing gums and any other chewable composition, dragee-cores or discrete (e.g., separately packaged) units of powder, granules, or suspensions or solutions in water or non-aqueous media Pharmacological preparations for oral use can be made by grinding the composition as disclosed herein, optionally while using a solid excipient, and processing the composition or mixture of granules, after adding suitable auxiliaries if desired, to obtain tablets or dragee cores.

Dragee cores are provided with suitable coatings. For this purpose, concentrated sugar solutions may be used which may optionally contain gum arabic, talc, polyvinyl pyrrolidone, carbopol gel, polyethylene glycol, silicon dioxide, titanium dioxide, lacquer solutions and suitable organic solvents or solvent mixtures. Dyestuffs or pigments may be added to the tablets or dragee coatings for identification or to characterize different combinations of active doses.

Pharmaceutical compositions, which can be used orally, include push-fit capsules made of HPMC or gelatin as well as soft, sealed capsules made of HPMC or gelatin and a plasticizer, such as glycerol or sorbitol. The push-fit capsules may contain the active ingredients in admixture with filler such as lactose, or silicon dioxide, binders such as starches, lubricants such as talc or magnesium stearate and, optionally, stabilizers. In soft capsules, the active ingredient may be dissolved or suspended in suitable liquids, such as fatty oils, liquid paraffin, or liquid polyethylene glycols. In addition, stabilizers may be added. Optionally, formulations for oral administration further include a protective coating, aimed at protecting or slowing enzymatic degradation of the preparation in the GI tract.

Composition unit dosage forms according to the present embodiments may, if desired, be presented in a pack or dispenser device, such as an FDA (the U.S. Food and Drug Administration) approved kit, which may contain one or more unit dosage forms containing the composition as disclosed herein. The pack or dispenser device may, for example, comprise metal or plastic foil, such as, but not limited to a blister pack. The pack or dispenser device may be accompanied by instructions for administration. The pack may also be accompanied by a notice associated with the container in a form prescribed by a governmental agency regulating the manufacture, use or sale of pharmaceuticals, which notice is reflective of approval by the agency of the form of the compositions for human administration. Such notice, for example, may be of labeling approved by the U.S. Food and Drug Administration for prescription drugs or of an approved product insert.

Unit dosage forms comprising the composition as disclosed herein can be prepared, placed in an appropriate container, and labeled for use as magnesium supplement, as described in further detail herein below.

According to some embodiments, the unit dosage form is identified (e.g., in the abovementioned instructions for administration) for use once or twice per day, optionally once per day.

According to some embodiments, the unit dosage form is identified (e.g., in the abovementioned instructions for administration) for use such that a daily dose consists of one or two units of the unit dosage form, and optionally one unit of the unit dosage form.

According to some embodiments, the unit dosage form is identified (e.g., in the abovementioned instructions for administration) for use before bed time.

In some embodiments, the unit dosage form comprises an amount of the composition as described herein which is equivalent to an amount of elemental magnesium of from about 50 mg to about 2000 mg, or from about 50 mg to about 1000 mg, or from about 50 mg to about 800 mg, or from about 100 mg to about 800 mg, or from about 300 to 800 mg or from about 400 to 600 mg, or is about 520 mg. Any intermediate value within the indicated ranges is contemplated.

Herein, the term "equivalent to an amount of elemental magnesium" refers to the amount of material (by weight) which is contributed by the magnesium element alone, excluding any other element in the composition.

In a particular embodiment, the unit dosage form comprises Vitamin $B_6$ in an amount of from 2 to 30 mg, more preferably from 5 to 10 mg, and most preferably of 10 mg.

A unit dosage form of the composition according to present particular embodiments further comprises Vitamin $D_3$ in an amount of from 400 to 4000 IU, in other words from 10 to 100 μg, more preferably from 400 to 1000 IU (10-25 μg).

In a further particular embodiment, the unit dosage form comprises Vitamin E in an amount of from 10 to 200 mg, more preferably from 20 to 100 mg, and most preferably 50 mg.

Optionally, a unit dosage form is designed so as to facilitate division of a unit dosage form into two half-unit dosage forms. For example, a pill, tablet or caplet may be scored so as to be readily broken in half.

In some embodiments, the pharmaceutical composition described herein, or the unit dosage forms described herein, are packaged in packaging material and identified for use as magnesium supplements, and/or in the treatment of a subject in need of magnesium supplementation.

A pharmaceutical composition oral dosage form releases an active ingredient or agent in the stomach (from where the agent can be absorbed after passing into the intestines) until the end of the gastric retention time, provided that the dosage form is capable of continuously releasing an active agent over such a period of time.

However, it is to be appreciated that the time during which the active agent is absorbed into the body may be longer than the gastric retention time, as absorption of the agent into the body may continue for a significant time period when the dosage form (or the remaining portion of the dosage form) is in the intestines. The duration of the time period during which absorption occurs after the dosage form has exited the stomach will depend on various factors, such as the length of the "absorption window" and the speed at which intestinal contents pass through the intestines.

When a pharmaceutical composition according to the present embodiments is orally administered, it releases free magnesium ions in the stomach.

By "free magnesium ions" it is meant $Mg^{2+}$ ions which are not complexed or otherwise bound to another moiety (as in the case of, for example, magnesium citrate or MgO).

It is assumed that under conditions of a human stomach, the free magnesium ions are generated by conversion of the administered magnesium salt into a magnesium chloride salt, which is completely dissolved in the aqueous environment and thus generates the free magnesium ions.

In some embodiments, the pharmaceutical composition unit dosage form as described herein is characterized as capable of generating free magnesium ions under physiological conditions of a human stomach, in an amount which is at least 50%, at least 60%, at least 70%, at least 80%, or at least 90%, and even 100% of its magnesium content.

In some embodiments, generation of magnesium ions in the stomach is effected during a time period that is equivalent to a retention time of the pharmaceutical composition in a human stomach.

In some embodiments, such a time period ranges from 30 minutes (0.5 hour) to 6 hours.

The capability of an exemplary pharmaceutical composition according to some embodiments of the present invention to dissolve in an acidic aqueous solution and thereby generate free magnesium ions has been demonstrated (see Example 2 in the Examples section the follows).

In some embodiments, a pharmaceutical composition unit dosage form as described herein is characterized as generating free magnesium ions in an amount which is least 50%, at least 60%, at least 70%, or at least 80%, of its magnesium content, when dissolved in an acidic aqueous solution for 45 minutes at room temperature.

In some embodiments, the acidic aqueous solution is a 0.1N HCl solution that is equivalent to the acidity of a stomach.

Some embodiments of the present invention are, therefore, based on the findings that compositions that comprise magnesium oxide and/or a hydrate form of magnesium oxide as described herein and/or magnesium hydroxide, including pharmaceutical compositions containing or consisting of such compositions, are characterized by a high dissolution rate and level in an aqueous solution, in which free magnesium ions are released. Without being bound by any particular theory, it is suggested that the high dissolution rate and level of such compositions attributes to the high level of magnesium cellular uptake, which can be represented as the value $[Mg^{2+}]i$, which results from orally administering magnesium oxide-type salt-containing compositions as described herein.

According to an aspect of some embodiments of the present invention, there is provided a pharmaceutical composition unit dosage form for oral administration, which comprises a magnesium oxide-type salt, including MgO and/or $Mg(OH)_2$ and/or $MgO.(H_2O)n$, wherein n is any value from 0.1 to 2, as described herein.

In some embodiments, such a composition is characterized as capable of generating free magnesium ions from at least 50% of its magnesium content under physiological conditions of a human stomach, as described herein.

In some embodiments, such a composition is characterized as capable of generating free magnesium ions from at least 50% of its magnesium content when dissolved in an acidic aqueous solution, as described herein, for 45 minutes at room temperature.

In some of these embodiments, the magnesium oxide-type salt comprises MgO. In some embodiments, it comprises a mixture of MgO and $MgO.(H_2O)n$, as described herein. In some embodiments, it comprises a mixture of MgO and Mg(OH)$_2$. In some embodiments, it comprises a mixture of MgO, Mg(OH)$_2$ and MgO.(H$_2$O)n. In some embodiments, it comprises solely MgO.(H$_2$O)n.

Preferably, the composition has a BET surface area ranging from 30 m$^2$/gram to 40 m$^2$/gram.

In some of these embodiments, one or more of the pharmaceutical composition unit dosage form(s) are packaged in a packaging material and identified for use as a magnesium supplement and/or in the treatment of a subject in need of magnesium supplementation.

Further according to embodiments of the present invention, there is provided a use of a composition as described herein in the manufacture of a magnesium supplement, which can optionally be used as a medicament for treating a subject in need of magnesium supplementation.

Further according to embodiments of the present invention, there is provided a composition or a pharmaceutical composition as described herein, which is identified for use as a magnesium supplement, and/or is identified for use in the treatment of a subject in need of magnesium supplementation.

Further according to some embodiments of the present invention, there is provided a magnesium supplement which comprises any of the compositions and pharmaceutical compositions as described herein.

Further according to some embodiments of the present invention, there is provided a method of treating a subject in need of magnesium supplementation, which is effected by administering to the subject a therapeutically effective amount of any of the compositions of the pharmaceutical compositions described herein.

In some embodiments, the method is effected by orally administering the composition or pharmaceutical composition.

In some embodiments, the therapeutically effective amount is such that is equivalent to from 50 to 2000 mg of elemental magnesium per day.

The therapeutically effective amount and regimen depend on the age, weight and health condition of the subject.

For example, generally healthy subjects typically require a therapeutically effective amount of elemental magnesium that ranges from 5 mg/kg body/day to 10 mg/kg body/day. Such an amount is accountable for maintaining a desired magnesium level and/or to prevent magnesium deficiency or hypomagnesaemia.

This amount can be elevated in generally healthy subjects that experience extensive physical efforts, for example, by exercising sport.

This amount can be elevated in generally healthy subjects that are under medication, as detailed herein.

This amount can further be elevated in generally healthy subjects who were diagnosed as suffering from magnesium deficiency, as detailed herein.

This amount can be elevated in subjects who suffer from a condition which is caused by magnesium deficiency, which causes magnesium deficiency and/or which is treatable by an elevated level of magnesium, as detailed herein.

In some embodiments, administering is effected once daily, however, can be effected from once up to 4 times a day.

By "magnesium deficiency", reference is made to serum magnesium level, cellular magnesium level and/or bone magnesium level.

In any of the aspects described herein, magnesium supplementation refers to maintaining a desired magnesium level and/or to prevent magnesium deficiency or hypomagnesaemia.

In any of the aspects described herein, treating a subject in need of magnesium supplementation refers to treating subjects who experience extensive physical efforts, as described herein, who take medications that typically cause magnesium deficiency, who are diagnosed as suffering from magnesium deficiency, and/or suffer from a condition which is caused by magnesium deficiency, which causes magnesium deficiency and/or which is treatable by an elevated level of magnesium, as detailed herein.

Exemplary subjects who can benefit from magnesium supplementation are those suffering from any one or more of hypomagnesaemia, coronary artery disease (CAD), chronic heart failure, diabetes mellitus, metabolic syndrome, an abnormal muscle excitability, a convulsive disorder, a psychiatric disturbance, a calcium and/or potassium abnormality, a chronic intoxication, alcoholism, drug abuse, renal wasting, stress, neurosis, a nervous disorder, an endocrine-metabolic disorder, malnutrition, constipation, preeclampsia, leg cramps, cerebral palsy, depression, asthma, a cardiovascular disease, an ischemic heart disease, cardiac arrhythmias, hypertension, pregnancy-induced hypertension, stroke, a cerebrovascular disease, osteoporosis, alcohol withdrawal, preterm labor, fatigue, renal stones, kidney stones, headache, migraine, altitude sickness, premenstrual syndrome, fibromyalgia, muscle weakness, insulin resistance, bronchospasms, hyperlipidemia, mitral valve prolapse, and neonatal encephalopathy.

Exemplary subjects who may benefit from magnesium supplementation are human beings of any age or condition, including fetuses, babies, adolescents, adults, elderly subjects, nursing and/or pregnant mothers, and healthy and/or sick patients.

It is expected that, during the life of a patent maturing from this application, many relevant additional conditions which are associated with magnesium deficiency or which are treatable by magnesium supplementation will be identified and the scope of conditions is intended to include any and all of newly identified conditions a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as defined hereinabove and as claimed in the claims section below find experimental support in the following non-limiting examples.

EXAMPLES

Reference is now made to the following examples, which, together with the above descriptions, illustrate some embodiments of the invention in a non-limiting fashion.

Example 1

MgO.(H$_2$O)n-Containing Formulation

Characterization:

A homogenous and stable granular powder containing MgO.(H$_2$O)n as co-product of high pure MgO, extracted from the Dead Sea, and Mg(OH)$_2$ obtained from ICL Industrial Products (Beer-Sheva Israel), with typical melting point, particle size, and analytical specifications, is utilized for formulating a magnesium-containing product as described herein.

One such exemplary magnesium-containing powder exhibits the following characteristics:
Purity of about 96.4%;
Loss on ignition of about 31.0%;
Bulk density of about 0.90 gram/mL;
Residual amount of non-Mg impurities of about 0.7%;
BET surface area of about 35 m$^2$/gram; and A particle size distribution, as determined by Laser Diffraction Method, and is expressed according to ASTM E 11-70 (1995) standard, as follows:
ASTM+30 mesh (0.595 mm)–8.0-20.0%
ASTM–30+60 mesh (0.595-0.250 mm)–60.0-70.0%
ASTM–60+100 mesh (0.250-0.149 mm)–5.0-25.0%
ASTM–100 mesh (0.149 mm)–1.0-8.0%

As shown herein, the particles vary in size but exhibit a d$_{70}$ (average particle size of 70% of the granules) of 30-60 mesh.

Figure 4:
FIG. 4 presents an optical image of a crystal of a magnesium-containing composition according to some embodiments of the present invention.

FIG. 4 presents a representative photograph of a granular magnesium-containing particle, showing it has a white gray color.

Formulation:

An oral unit-dosage form containing magnesium oxide hydrate of the present invention is prepared by compacting a powder as described herein, optionally mixed with additional active and non-active ingredients, into tablets.

In an exemplary procedure, tablets were prepared by direct compaction (batch size of 200 kg) using an 8-station Riva Piccola tablet machine formatted with 11 mm round, standard concave punches, to a target tablet weight of 1000 mg±3%.

Thus, a granular composition containing Mg.(H$_2$O)n, optionally mixed with Mg(OH)$_2$ and/or MgO (900 mg), Microcrystalline cellulose (200 mg), Copovidone (50 mg) and Crospovidone (0.0-20 mg) was blended in a low-shear mixer for five minutes. Colloidal silicon dioxide (5 mg) and optionally Magnesium stearate (5 mg) were then added and the resulting mixture was blended for an additional two minutes. The final blend was passed through a 0.8 mm sieve and the obtained powder was compacted into tablets using the Piccola press, as described herein, at an applied force of 20-22 kN.

Coated tablets are prepared by applying an enteric coating, using acceptable polymers like Eudragit L-30 D-55, hydroxy propyl methylcellulose phthalate (HPMCP), cellulose acetate phthalate and Acryl-EZE®, to achieve 5% weight gain of the coating.

In an exemplary process, tablets were film-coated using an O'Hara LabCoat IIX side-vented coating machine fitted with a 15" coating pan and a Schlick ABC two-fluid spray nozzle. The general process conditions used were as follows:
Tablet charge (kg) 2.0;
Solids content in coating suspension 12.5% w/w;
Target weight gain 3% w/w;
Inlet air temperature 60° C.;
Pan speed 15 rpm;
Inlet air volume 255 m$^3$·h$^{-1}$;
Atomizing air pressure 1.3 bar;
Pattern air pressure 2.3 bar;
Spray rate 15 g·min$^{-1}$.

Alternatively, a granular composition, containing Mg.(H$_2$O)n, optionally mixed with Mg(OH)$_2$ and/or MgO (900 mg), is formulated into HPMC or Gelatin Capsules (e.g., No. 00), using silicon dioxide as an excipient, in an amount of up to 5 mg per 1 gram composition (per 1 capsule). Optionally, a composition is formulated to contain at least 50 mg of Vitamin E, at least 10 mg of Vitamin B$_6$ and preferably 400 IU of Vitamin D$_3$.

Example 2

Dissolution Tests

The solubility of magnesium-containing capsules was tested in an assay performed according to USP specifications. In this assay, the solubility of a variety of magnesium-containing samples was tested as a function of the magnesium salt/complex used and the type of the formulation.

A round-bottomed flask containing 100 ml 0.1 N hydrochloric acid (HCl), which is the equivalent to stomach acidity, was heated to 37° C. A tested magnesium-containing sample was then placed inside the flask and stirred at 75 rpm by a mechanical agitator. After 45 minutes, the quantity of dissolved magnesium was measured by titration with sodium hydroxide (0.2 mol·dm$^{-3}$).

The results are presented in Table 1 below and show that the capsules containing magnesium oxide and/or a hydrate thereof exhibited the highest solubility of all types tested, both percentagewise, as the percent of magnesium (relative to the amount of the elemental magnesium in the capsule) and on an absolute scale (of the quantity of dissolved magnesium).

TABLE 1

| Quantity of Magnesium which dissolved (mg) | Percent of Magnesium dissolved as measured by Assay | Amount of Elemental Magnesium per unit (mg) | Magnesium Source | Type of encapsulation | Company Name |
|---|---|---|---|---|---|
| 323 | 87% | 370 | Powdered MgO and/or a hydrate form thereof | Capsule, 625 mg | Naveh Pharma |
| 158 | 63% | 250 | Magnesium Citrate | Capsule | Solgar XXX |
| 44 | 45% | 98.6 | Magnesium Citrate | Chewable Tablet | Diasporal |

Figure 5A:
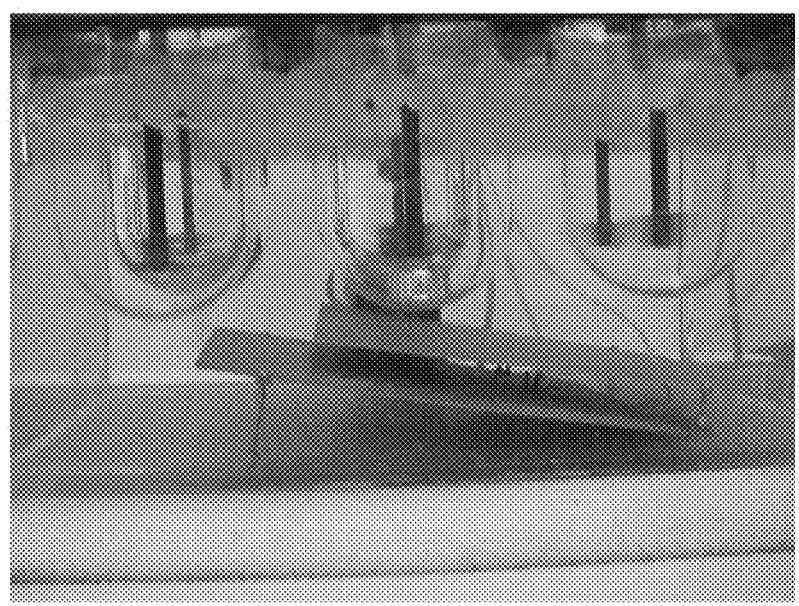
FIGS. 5A-5C present images of a dissolution assay testing dissolution of various magnesium-containing samples.
Figure 5B:
Figure 5C:
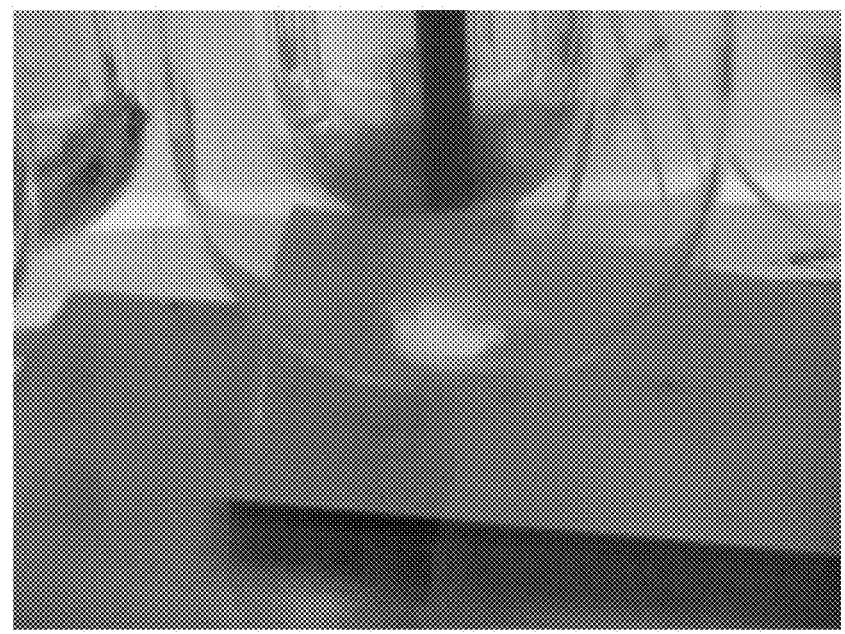

Optical images of the tested solutions are shown in FIGS. 5A-C. FIG. 5A shows the experimental setup; a magnesium sample can be seen in the center flask. The clear solution is indicative of complete dissolution. FIG. 5B shows a close-up of the Solgar capsules, containing magnesium citrate. FIG. 5C shows a close-up of Diasporal chewable tablets, containing magnesium citrate.

The examples set forth above are given to provide those of skill in the art with disclosure and description of how to make and use various embodiments of the methods disclosed herein, and is not intended to limit the scope of the invention.

A composition and/or method described herein may be useful for purposes described herein, such as maintaining and/or improving in humans the health conditions related to magnesium deficiency.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be interpreted as necessarily limiting.

The scope of the invention is to be interpreted in accordance with the substance defined in the following claims.

REFERENCES

Ahdjoudj J., Minot C. Adsorption of H2O on metal oxides: a periodic ab-initio investigation. Surface Science. 1998; 402-404 (1-3):104-109

Altura B. T., Wilimzig C., Trnovec T., Nyulassy S., Altura B. M. Comparative effects of a Mg-enriched diet and different orally administered magnesium oxide preparations on ionized Mg, Mg metabolism and electrolytes in serum of human volunteers. J Am Coll Nutr. 1994; 13:447-454

Aranovich, L. Y., Newton, R. C. (1996) H$_2$O activity in concentrated NaCl solutions at high pressure and temperatures measure by the brucite-periclase equilibriium. Contributions to Mineralogy and Petrology. 1996; 125: 200-212

Ball M. C., Taylor H. F. W. The dehydration of brucite. Mineral. Mag. 1961; 32:754-766

Barnes H. L., Ernst W. G. Ideality and ionization in hydrothermal fluids. The system MgO—H2O—NaOH. American Journal of Science. 1963; 261:129-150

Centers for Disease Control and Prevention. Hyattsville, Md.: National Center for Health Statistics, 1994:1-28

Coudray C., Rambeau M., Feillet-Coudray C, Gueux E, Tressol J. C., Mazur A., Rayssiguier Y. Study of magnesium bioavailability from ten organic and inorganic Mg salts in Mg-depleted rats using a stable isotope approach. Magnes Res. 2005; 18(4):215-23

Fine K. D., Santa Ana C. A., Porter J. L., Fordtran J. S. Intestinal absorption of magnesium from food and supplements. J Clin Invest. 1991; 88(2):396-402

Fingl E., Woodbury D. M. General Principles, in The Pharmacological Basis of Therapeutics, 5th ed., ed. L. S. Goodman and A. Gilman. Chap. 1: 1-46, 1975

Firoz M., Graber M. Bioavailability of US commercial magnesium preparations. Magnes Res. 2001; 14: 257-62

Irving E., Emslie R. F., Park J. K. Paleomagnetism of the Harp Lake Complex and associated rocks. Canadian Journal of Earth Sciences. 1977; 14(6):1187-1201

Jost H., Braun M., Carius Ch. The role of reactivity in syntheses and the properties of magnesium oxide. Solid State Ionics. 1997; 101-103(1):221-228

Johnson M. C., Walker D. Brucite [Mg(OH)2] dehydration and the molar volume of $H_2O$ to 15 GPa. American Mineralogist. 1993; 78:271-284

Kanzaki M. Dehydration of brucite (Mg(OH)2) at high pressures detected by differential thermal analysis. Geophysical Research Letters. 1991; 18(12):2189-2192

Leinenweber K., Utsumi W., Tsuchida Y., Yagi T., Kurita K. Unquenchable High-Pressure Perovskite Polymorphs of MnSnO3 and FeTiO3. Physics and Chemistry of Minerals. 1991; 18:244-250

Lindberg J. S., Zobitz M. M., Poindexter J. R., Pak C. Y. Magnesium bioavailability from magnesium citrate and magnesium oxide. Journal of the American College of Nutrition. 1990; 9:48-55 2

Liu X. H., Zhang X. G., Wang X. Y., Lou N. Q. Solvation of magnesium oxide clusters with water in direct laser vaporization. International Journal of Mass Spectrometry and Ion Processes. 1997; 171(1-3):L7-L11

L'vov B. V et al. Mechanism of thermal decomposition of magnesium hydroxide. Thermochimica Acta 1998; 315 (2): 135-143

Meyer, J. W and Yang, I. Some observations in the system MgO—H2O. American Journal of Science. 1962; 260: 707-717

Muhlbauer B., Schwenk M., Coram W. M., Antonin K. H., Etienne P., Bieck P. R., Douglas F. L. Magnesium-L-aspartate-HCl and magnesium-oxide: bioavailability in healthy volunteers. Eur J Clin Pharmacol. 1991; 40:437-438

Ross J. R., Dargan P. I., Jones A. L., Kostrzewski A. A case of hypomagnesaemia due to malabsorption, unresponsive to oral administration of magnesium glycerophosphate, but responsive to oral magnesium oxide supplementation. Gut. 2001; 48(6):857-8

Saris N. E, Mervaala E., Karppanen H., Khawaja J. A., Lewenstam A. Review Magnesium. An update on physiological, clinical and analytical aspects. Clin Chim Acta. 2000; 294(1-2):1-26

Schramke J. A., Kerrick D. M., Blencoe J. G. Experimental determination of the brucite=periclase+water equilibrium with a new volumetric technique. American Mineralogist. 1982; 67:269-276

Schuette S. A., Janghorbani M., Young V. R., Weaver C. M. Dysprosium as a nonabsorbable marker for studies of mineral absorption with stable isotope tracers in human subjects. J Am Coll Nutr. 1993; 12(3):307-15

Schuette S. A., Lashner B. A., Janghorbani M. Bioavailability of Magnesium Diglycinate vs Magnesium Oxide in Patients with Ileal Resection. J Parenter Enteral Nutr. 1994; 18:430-435

Seelig M. S. The requirement of magnesium by the normal adult. Am J Clin Nutr. 1964; 6:342-390

Seelig M. S. Cardiovascular consequences of magnesium deficiency and loss: Pathogenesis, prevalence and manifestations-Magnesium and chloride loss in refractory potassium repletion. The American Journal of Cardiology. 1989; 63:G4-G21

Seelig M. S., Rosanoff A. The magnesium factor. Avery, N.Y., 2003. Avery Publishers, August 2003

Shechter M., Bairey Merz C. N., Stuehlinger H. G., Slany J., Pachinger O., Rabinowitz B. Effects of oral magnesium therapy on exercise tolerance, exercise-induced chest pain, and quality of life in patients with coronary artery disease. Am J Cardiol. 2003; 91:517-521

Shechter M. Magnesium and cardiovascular system. Magnes Res. 2010; 23: 60-72

Shinobu Yamaoka, Osamu Fukunaga, Shiroku Saito. Phase Equilibrium in the System MgO—H2O at High Temperatures and Very High Pressures. Journal of the American Ceramic Society. 1970; 53(4):179-181 3

"The Merck Manual Home Health Handbook," Merck & Co. Inc. 3rd edition, 2009, Chapter 10

Xin Z., Tucker W. B., Hemken R. W. Effect of Reactivity Rate and Particle Size of Magnesium Oxide on Magnesium Availability, Acid-Base Balance, Mineral Metabolism, and Milking Performance of Dairy Cows. Journal of Dairy Science. 1989; 72(2):462-470

Yamaoka S., Fukanaga O., Saito, S. Phase equilibrium in the system MgO—H2O at high temperatures and very high pressures. Journal of the American Ceramic Society. 1970; 53:179-181

The invention claimed is:

1. A method of treating a pregnant woman suffering from pre-eclampsia, the method comprising orally administering to the pregnant woman, daily, a therapeutically effective amount of a composition comprising a hydrate form of magnesium oxide, denoted as $MgO.(H_2O)n$, at a concentration ranging from 1 to 100 weight percent (wt %), where n is any value from 0.1 to 2, wherein an amount of elemental magnesium in said therapeutically effective amount is in a range of from 500 mg to 2000 mg per day.

2. The method of claim 1, wherein said composition comprises:

Magnesium oxide hydrate $MgO.(H_2O)n$, at a concentration ranging from 1 to 100 wt %, wherein n in any value from 0.1 to 2;

MgO at a concentration ranging from 0 to 99 wt %; and $Mg(OH)_2$ at a concentration ranging from 0 to 99 wt %.

3. The method of claim 1, wherein said composition comprises:

Magnesium oxide hydrate $MgO.(H_2O)n$, at a concentration ranging from 1 to 100 wt %, wherein n in any value from 0.1 to 2, and MgO at a concentration ranging from 0 to 99 wt %; or Magnesium oxide hydrate $MgO.(H_2O)n$, at a concentration ranging from 1 to 100 wt %, wherein n in any value from 0.1 to 2, and $Mg(OH)_2$, at a concentration ranging from 0 to 99 wt %; or Magnesium oxide hydrate $MgO.(H_2O)n$, at a concentration ranging from 1 to 100 wt %, wherein n is any value from 0.1 to 2, and $Mg(OH)_2$ at a concentration ranging from 0 to 99 wt %, and MgO, at a concentration ranging from 0 to 99 wt %.

4. The method of claim 1, wherein n ranges from 0.3 to 1.

5. The method of claim 1, wherein a concentration of said $MgO.(H_2O)n$ in said composition is selected from the group including: at least 10 wt %, at least 20 wt %, at least 30 wt %, at least 40 wt %, at least 50 wt %, at least 60 wt %, at least 70 wt % or at least 80 wt % of a total weight of the composition.

6. The method of claim 1, wherein said composition is in a form of a plurality of particles.

7. The method of claim 6, wherein said particles have a BET surface area ranging from 30 $m^2$/gram to 40 $m^2$/gram.

8. The method of claim 1, wherein said composition further comprises a pharmaceutically acceptable carrier.

9. The method of claim 1, wherein said composition further comprises at least one additional active agent.

10. The method of claim 9, wherein said at least one additional agent is selected from Vitamin D, Vitamin $B_6$, and Vitamin E.

11. The method of claim 1, wherein said composition is formulated as a unit dosage form for oral administration, wherein an amount of elemental magnesium in said unit dosage form ranges from 500 mg to 2000 mg, wherein said unit dosage form is administered daily.

12. The method of claim 1, wherein said composition is characterized as capable of generating free magnesium ions from at least 50% of said composition under physiological conditions of a human stomach.

13. The method of claim 1, wherein said composition characterized as generating free magnesium ions from at least 50%, or at least 80%, of said composition when dissolved in an acidic aqueous solution for 45 minutes at room temperature.

* * * * *